United States Patent [19]
Syrop et al.

[11] Patent Number: 5,562,105
[45] Date of Patent: Oct. 8, 1996

[54] FLUID MOTION JAW EXERCISING DEVICE

[75] Inventors: Steven Syrop, Chappaqua, N.Y.;
Howard Israel, 47 Part Cir., Great Neck, N.Y. 11024

[73] Assignees: Steven B. Syrop, Chappaqua; Howard Israel, Great Neck, both of N.Y.; Edward C. Meyers, Boca Raton, Fla.

[21] Appl. No.: 495,541
[22] PCT Filed: Feb. 1, 1993
[86] PCT No.: PCT/US93/00963
§ 371 Date: Jul. 26, 1995
§ 102(e) Date: Jul. 26, 1995
[87] PCT Pub. No.: WO94/17770
PCT Pub. Date: Aug. 18, 1994

Related U.S. Application Data

[63] Continuation-in-part of Ser. No. 738,105, Jul. 30, 1991, Pat. No. 5,183,057.
[51] Int. Cl.⁶ .............................. A61G 15/00; A61C 5/14
[52] U.S. Cl. ............................. 128/845; 128/861; 433/69
[58] Field of Search ................................. 128/845, 846, 128/857, 858–862, 62 A; 2/2; 433/69, 229; 446/197, 198

[56] References Cited

U.S. PATENT DOCUMENTS

| | | | |
|---|---|---|---|
| 2,566,557 | 9/1951 | Danielson | 128/863 |
| 3,315,672 | 4/1967 | Cunningham | 128/863 |
| 3,545,125 | 12/1970 | Okuma . | |
| 3,625,207 | 12/1971 | Agnew | 128/146.2 |
| 3,997,157 | 12/1976 | Meyer | 446/197 |
| 4,928,710 | 5/1990 | Campbell | 128/861 |
| 4,932,867 | 6/1990 | Ueno | 433/69 |

*Primary Examiner*—Michael A. Brown
*Attorney, Agent, or Firm*—Frishauf, Holtz, Goodman, Langer & Chick

[57] ABSTRACT

A method and apparatus are disclosed for exercising small joints such as the temporomandibular joint connecting the upper and lower jaws, fingers and toes of a user and for toning jaw muscles of the user. First and second members coupled together so that at least one of the members is movable relative to the other member. An expandable and contractible fluid reservoir is positioned between the first and second members so that the first and second members will move relative to each other as the expandable and contractible reservoir expands and contracts. At least one of the members is then positioned to exercise the joint, specifically to exercise the jaw. To use the apparatus, the user places the first and second members gently into the mouth and then squeezes a fluid source connected to the expandable and contractible reservoir to expand and contract the reservoir thereby moving the jaws or joint to be exercised. When used for toning jaw muscles, the expandable and contractible fluid reservoir is prevented from contracting as the user bites down on the first and second members. This prevention of contraction creates a resistance against which the biting down by the user acts. This resistance tones jaw muscles of the user as the user repeatedly bites down against the resistance. A settable squeezing device can provide setting squeezing pressures to the fluid source to provide a controlled expansion of the expandable and contractible fluid reservoir and provide controlled resistance against the biting down by the user.

38 Claims, 6 Drawing Sheets

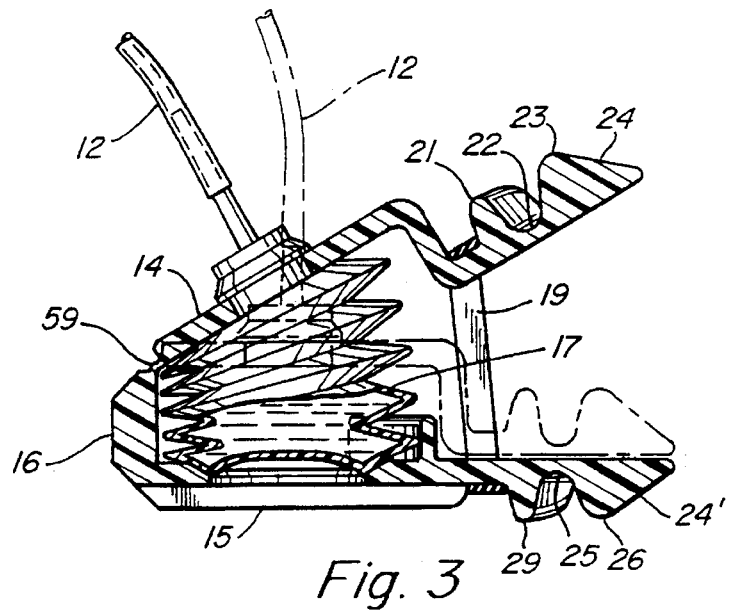
Fig. 3
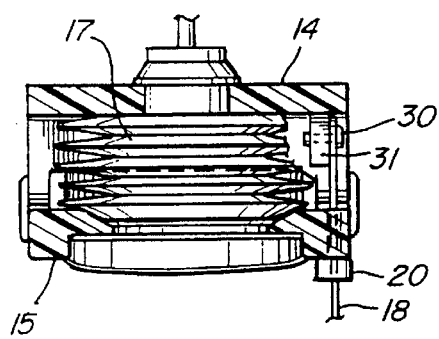
Fig. 4
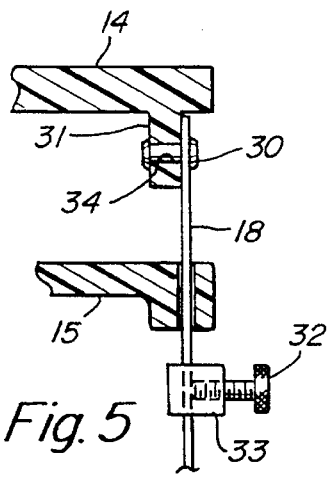
Fig. 5
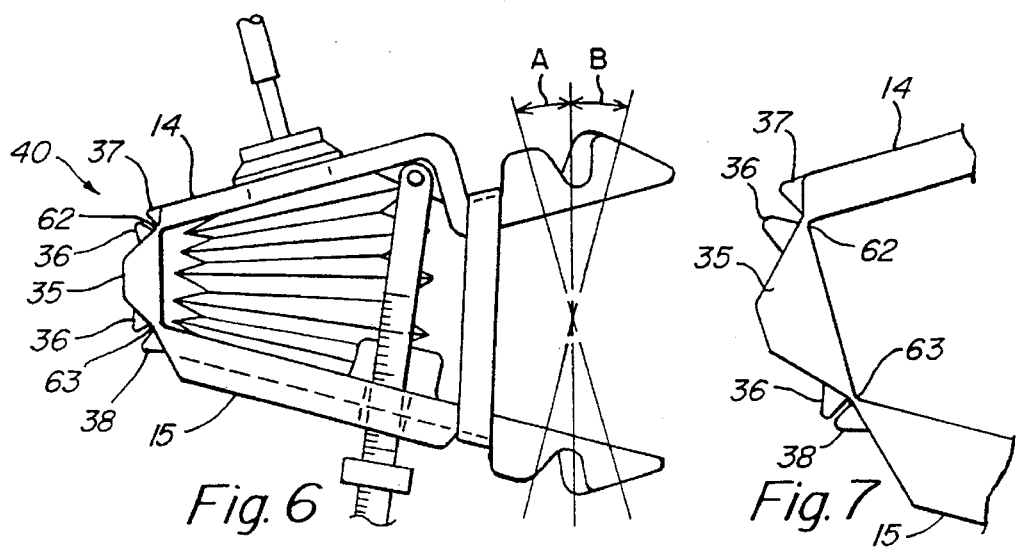
Fig. 6
Fig. 7

FLUID MOTION JAW EXERCISING DEVICE

This application is a continuation in part of Ser. No. 07/738,105 filed Jul. 30, 1991, now U.S. Pat. No. 5,183,057.

BACKGROUND OF THE INVENTION

1. Field of the Invention

This invention relates generally to joint exercising apparatus and more particularly to jaw exercising apparatus for use in exercising the jaws of patients who suffer from Temporomandibular Joint (TMJ) problems. The apparatus is also useable for toning jaw muscles. The present invention is also useable to prevent scarring to the TMJ following radiation to the head and neck of a patient.

TMJ problems are relatively common in the general population. Epidemiological studies have provided evidence that anywhere from 3 to 18% of the population developed symptoms characteristic of temporomandibular joint disorders at some time in their lives.

1. Description of the Prior Art

It is known from the prior art that continuous passive motion (CPM) can be used to manage joint disorders including the temporomandibular joint. Joint motion provides cartilage nutrition, stimulates regeneration of articular cartilage and reduces pain and edema. Motion is extremely important to normal joint physiology. Motion permits maintenance of healthy articular cartilage by allowing nutrients in the synovial fluid to diffuse through the surface. It has been shown that motion is also extremely important in the prevention of adhesions in the joint following injury or surgery. Motion has also been shown to reduce pain and edema in a joint that has undergone surgery or trauma. Gradual mobilization exercises have been used to help regain normal range of motion in patients with myalgia and myositis of the masticatory muscles. Specifically exercising the TMJ is beneficial:

following temporomandibular joint surgery to reduce adhesions, pain and edema and to increase the range of motion;

following intermaxillary fixation (jaws wired closed) in patients treated with jaw fractures or orthognathic surgery, to increase the range of motion and reduce pain and edema;

following treatment of facial infections that result in reduced jaw opening;

following acute trauma (blow to the jaw) or chronic trauma (grinding or clenching of teeth) to the joint, to reduce pain, edema, encourage cartilage nutrition and restore normal range of motion;

if the patient suffers from myositis and myalgia, to gradually restore the range of motion; and following any oral and maxillo facial surgery (such as removal of wisdom teeth) which may result in a period of decreased jaw opening.

Temporomandibular joint exercisers known in the prior art were directed to mechanical and electro mechanical, relatively complex bulky devices which were expensive and frequently required individual adjustment of the device to fit a person's mouth, thus limiting use of such exercisers to non-routine TMJ problems.

SUMMARY OF THE INVENTION

An object of the present invention is to provide a fluid motion device (FMD), that is a passive motion device, that provides controlled motion to the temporomandibular joint as well as the surrounding soft tissues, muscles, tendons and ligaments.

Another object is to provide such a device which uses an hydraulic mechanism which permits gentle gradual control of jaw movement and enables biofeedback to insure that the temporomandibular joint movement is controlled by the patient within a predetermined limited range of movement.

A further object of the present invention is to provide a safe simple method for toning jaw muscles, exercising small joints and to provide a simple, inexpensive fluid motion device (FMD) for use in exercising small joints (such as fingers, toes and the TMJ) and for toning jaw muscles that can be used readily by a user, patient, practitioner or physical therapist at home, or, in a medical or dental office and in a variety of other situations, and wherein the method and apparatus prevents the user or patient from being injured by utilization of the method and apparatus.

Another object of the present invention is to provide a simple, inexpensive light weight passive motion device that can be used by most users or patients without requiring individual adjustments. The jaw exerciser could be sold by prescription; the hand exerciser and jaw muscle toner could be sold over the counter, possibly without prescription, for finger exercisers for patients suffering from arthritis and other small joint problems or for use by persons who wish to enhance jaw muscle tone.

BRIEF DESCRIPTION OF THE DRAWINGS

FIG. 3 is a sectional view taken along line 3—3 in FIG. 2 of the bellows portion of the present invention which is used to separate the jaws of the patient or user.

FIG. 4 is a sectional view taken along line 4—4 in FIG. 2.

FIG. 5 is a sectional view of an alternate stop device for limiting the maximum opening provided by the hydraulic mechanism of FIG. 2.

FIG. 6 is a schematic view of an alternate hinge mechanism for the hydraulic bellows shown in FIG. 3, which has a double hinge to enable the apparatus to compensate for overbite or underbite or a patient or user.

FIG. 7 is a schematic view of the double hinge mechanism of FIG. 6, which shows the details of the protrusions on each of the double hinges to limit maximum movement of the bellows relative to the hinges.

DESCRIPTION OF THE EMBODIMENTS

Figure 1:
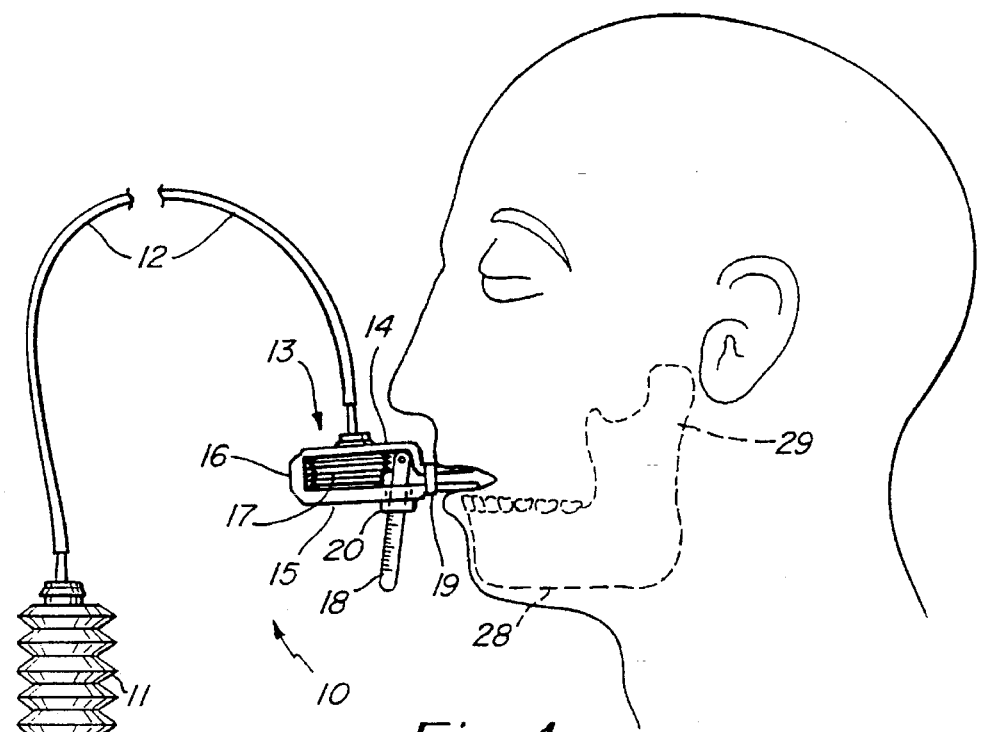
FIG. 1 is a side schematic view in elevation, showing an apparatus of the present invention for use in connection with TMJ, and the positioning of the apparatus in the mouth of a user or patient.

FIG. 1 discloses the components of the hydraulic mechanism of the present invention when positioned to exercise the temporomandibular joint (TMJ) of a person or when positioned to tone the jaw muscles of a user.

Figure 2:
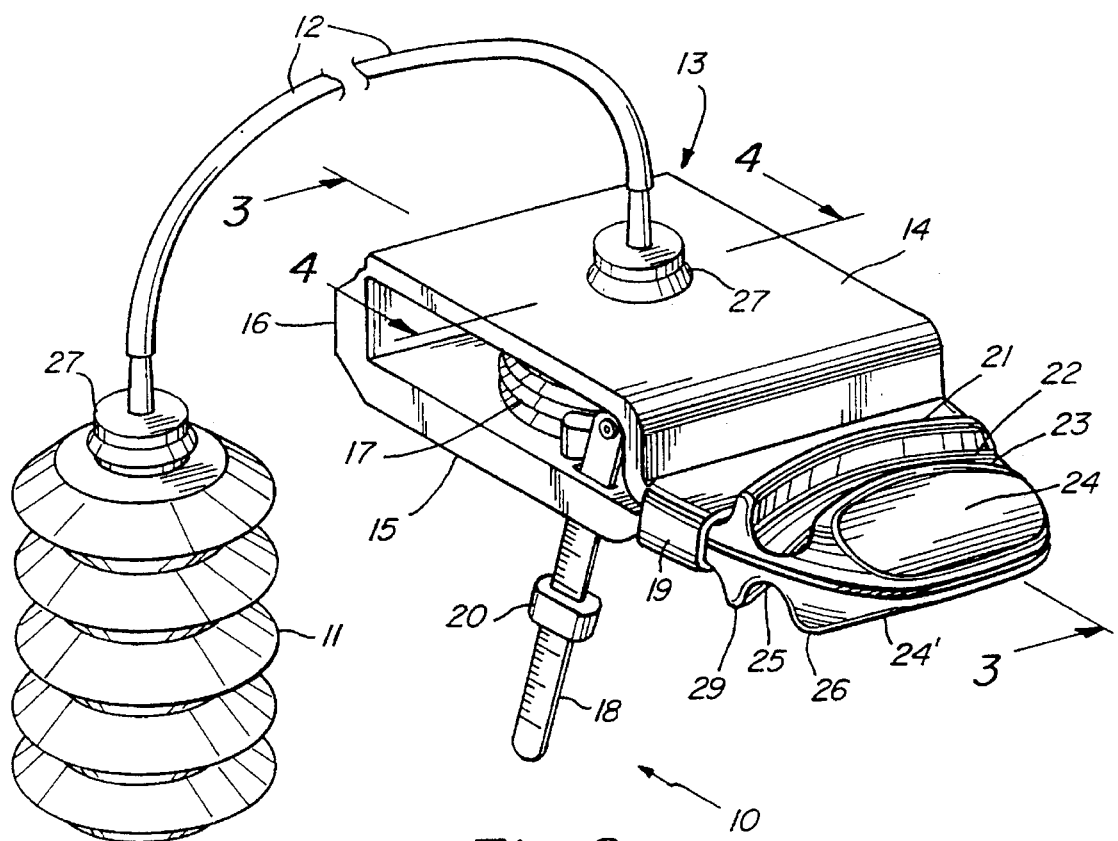
FIG. 2 is a perspective view of the hydraulic mechanism of the present invention.

Referring to FIGS. 1 and 2 the hydraulic apparatus 10, includes the following principal components: a fluid source 11; a flexible tube 12 in fluid communication with the fluid source 11 attached to fluid source 11 at one end thereof by coupling 27; and a motion control apparatus 13 attached to the other end of said flexible tube 12 by another coupling means 27. The motion control apparatus 13, includes an upper member 14 and a lower member 15, which are pivotally connected together at one end thereof by hinge portion 16. A flexible expandable bellows 17 is positioned between the upper and lower members and is in fluid communication with the flexible tube 12 via the coupling 27. The coupling 27 can screw onto a corresponding threaded portion on fluid source 11 and bellows 17 or upper member 14. The fluid source 11 can be a bellows, or any other shape which can facilitate controlled squeezing. The couplings 27 can be unscrewed to fill the device 10 with a fluid. Device 10 is preferably formed from a moldable plastic. The fluid source 11 and tube 12 and bellows 17 can be filled with a fluid and then permanently sealed to each other to provide a fluid-tight fluid path which never has to be refilled. The fluid source 11 may be replaced with an infusion pump (see FIG. 9) to permit continuous passive motion in the immediate post operative period for a hospitalized patient. Adjustable measurement means, such as ruler 18 can be positioned and fastened to upper member 14 to facilitate measurement of the maximum permissible mouth opening for the particular patient. Ruler 18 has stop means 20 for selecting the maximum permissible opening for the mouth, of the patient or user, and to act as a stop to prevent further opening of the mouth. An elastic member 19 holds the upper member 14 and the lower member 15 together on the side of motion control apparatus 13, which is the side opposite from hinge portion 16.

As shown in FIG. 2, an integral portion of the upper member 14 is the end portion thereof which has formed thereon a first ridge 21 and a second ridge 23, which are separated by a recess 22. The two ridges and recess are shaped to accommodate the upper teeth of the patient or user when positioned in the mouth. A sloping ramp portion 24 at the free end of the upper member is designed to generally fit into the mouth of a patient or user, behind the front teeth. Similarly, the lower member 15 has an extended integral free end portion thereof (at the end away from the hinge 16), which includes a first ridge 29, a second ridge 26, and a recess 25 formed between the ridges 24 and 26. The ridges 24 and 26 with the intervening recess 25 are shaped to accommodate and retain the lower teeth of the patient or user when the motion control apparatus is positioned in the mouth. The front free end portion of the lower member includes a sloping portion 27, shaped to generally fit into the mouth of a patient or user when the motion control apparatus is positioned in the patient's or user's mouth.

In operation, when the FMD is in the closed position (as shown in FIG. 2), the patient or user gently slides the device into his/her mouth along gently inclined ramps 24 and 27 until the upper and lower teeth fit into recesses 22 and 25. The fluid source 11 and bellows 17 and tubing 12 are then filled with fluid (if they were not permanently or previously filled) and the patient holds the fluid source (bellows) 11 in one hand. By squeezing the bellows 11 fluid is transferred to bellows 17 located between the upper and lower members of the FMD and thus, causes a gentle, fluid controlled separation of the lower jaw from the upper jaw. Since the patient or user is controlling the motion of the fluid, which is gradual, sudden jaw movement is avoided, preventing injury to the joint and surrounding structures. The elastic means 19 holding the free ends of the upper and lower members together, permits a passive return of the jaws to a closed mouth position. The fluid source 11 is filled with a fluid preferably water, and is coupled to tube 12 with a coupling device 27. The tube 12 is in fluid communication with the fluid source 11. The other end of tube 12 is coupled to the motion control apparatus 13 by another coupler 27 which, in turn, is in fluid communication with bellows 17 such that fluid, can move from the fluid sources 11 through the tube 12 to the bellows 17, and in the reverse direction from the bellows 17 through the tube 12 back into the fluid source 11 when pressure on fluid source 11 is released and the elastic means 19 passively returns members 14 and 15 to their original unseparated position.

In operation, when the fluid source 11 is filled with a fluid, pressure exerted on the fluid source 11 by the patient or user will force fluid through the tube 12 into the bellows 17. The bellows because of the hinge portion 16 can only open, as shown in 3, to separate the top member 14 and bottom member 15. The maximum opening between the top and bottom members is measured by the ruler 18 and guide 20 slidable on ruler 18. When the exerted pressure is released on the fluid source 11 the elastic means 19 positioned to hold the upper and lower members 14 and 15 together will exert a force sufficient to close the gap between the members created when fluid was forced into bellows 17. This action by the elastic member 19 in combination with the return of fluid source 11 to its original shape will allow fluid to flow out of bellows 17 back into the fluid source 11 until pressure is, again, exerted on the fluid source 11 by the patient or user. When pressure is exerted and released repeatedly on the fluid source 11, shown in FIG. 1, the lower jaw of the patient, schematically shown at 28, will move relative to the upper jaw which, in turn, will cause the mouth of the patient to repeatedly open and close, thereby exercising the temporomandibular joint and surrounding soft tissue schematically shown at 29 in FIG. 1.

In FIGS. 1 and 2, maximum movement of the upper and lower members 14 and 15 is measured by the ruler 18 and guide 20. FIG. 3 is a sectional view of the motion control apparatus 13 of FIGS. 1 and 2, taken along the line 3—3 in FIG. 2. The solid line showing of upper member 14 in FIG. 3 shows the upper member 14 in its open position. The dashed lines in FIG. 3, show the upper member 14 when it is in its closed position relative to lower member 15.

Hinge 16, which can also be a living hinge, connects upper member 14 and lower member 15, together and permits relative movement of said members 14 and 15 relative to each other. Portion 59 of hinge 16 can be a hinge member attached on one side to upper member 14 and on the other side to hinge portion 16 to enable the upper member to move relative to the hinge portion 16 and lower member 15. As shown in FIG. 3 hinge portion 16 is fixed to member 15 to prevent movement therebetween. Portion 59 may be made of a plastic material which is fixed or otherwise attached to upper member 14 and which flexes as upper member 14 is moved relative to hinge portion 16.

FIG. 4, is a sectional view of the motion control apparatus 13 taken along the line 4—4 in FIG. 2. In FIG. 4, the upper member 14 and the lower member 15 are in the closed position.

In FIG. 4, the mounting means 30 for mounting ruler 18 on upper member 14 is schematically shown as a rivet or pin 30; however, other mounting means such as a screw and nut may be used.

FIG. 5 shows an alternate embodiment for the ruler 18 of FIGS. 1 and 2 mounted on upper member 14 and lower member 15. As shown in FIG. 5, the upper member 14 has a projecting portion thereof 31 formed integrally therewith. The rivet 30 or the like is mounted through the upper end of the ruler 18 through an aperture 34 formed in projection 31 of upper member 14 and a rivet or pin 30 is mounted in the aligned apertures. The ruler 18 slidably fits through an aperture formed in lower member 15; a slide 33 is mounted on ruler 18, and a thumbscrew 32 fits into an aperture in slide 33 which cooperates to set the maximum opening position for upper and lower members 14 and 15. Thumbscrew 32 and slide 33 are alternates to the ruler 18 and guide 20 shown in FIGS. 1 and 2. Alternately, guide 20 may be provided with a stop means to prevent guide 20 from moving.

FIG. 6 discloses an alternate hinge 40 for the hinge 16 shown in FIGS. 1 and 2. In FIG. 6, the hinge 40 comprises a central member 35. Hinge means 62 connects upper member 14 to the central member 35; hinge means 63 connects lower member 15 to central member 35. This configuration provides a double acting hinge means 40 which permits movement respectively by upper member 14 and lower member 15 in both the horizontal and vertical planes. Movement laterally permits the motion control apparatus 13, to move within the motion limits A and B shown in FIG. 6 for hinge means 62, 63 to accommodate for overbite or underbite of a patient or user without individual adjustment. Central member 35, and hinge means 62, 63, may be formed integrally with each other as well as integrally with the upper member 14 and lower member 15. Protrusions 37 and 38 can be provided to limit the movement of hinge means 62, 63 and are respectively formed on upper member 14 and lower member 15 adjacent to but spaced from the respective upper and lower protrusions 36 formed on the central hinge member 35. The space between protrusions 36, formed on the central hinge member 35 and the respective protrusions 37 and 38, provide some "play" at the hinge 40 to permit the upper and lower members 14, 15 of the motion control apparatus 13 to adjust laterally within a range determined by the protrusions for overbite and underbite by a patient or user using the device. Compensation for upper jaw overbite would be provided for by the hinge 40 by permitting movement shown by the arrow B in FIG. 6. Compensation for underbite of the upper jaw relative to the lower jaw would be provided for by the hinge 40 by permitting the relative movement shown by the arrow A in FIG. 6. The hinge 40 can compensate for overbite or underbite, as well as for badly aligned jaws and teeth within a range which would accommodate a large number of patients or users without requiring special adjustment of the motion control apparatus 13 to accommodate specific individual needs.

FIG. 7 is an enlarged view of the hinge 40 shown in FIG. 6. FIG. 7 shows that the gap between the protrusion 38 on bottom member 15 and the protrusion 36, formed at the bottom of central hinge member 35, has been closed while the gap between the protrusion 37 on top member 14 and, the top protrusion 36 on central hinge member 35, still remains open. The protrusions 36, 37 and 38 can thus act as lateral motion limit control members, which limit the amount of motion between the protrusions 36, 37 and 38. In other words, when the gap between protrusions 36 and 37 is closed, no further movement by that portion of the hinge is possible, whereas, the hinge 40 shown in FIG. 7 can permit further movement between protrusion 37 and upper protrusion 36 of central member 35.

Figure 8:
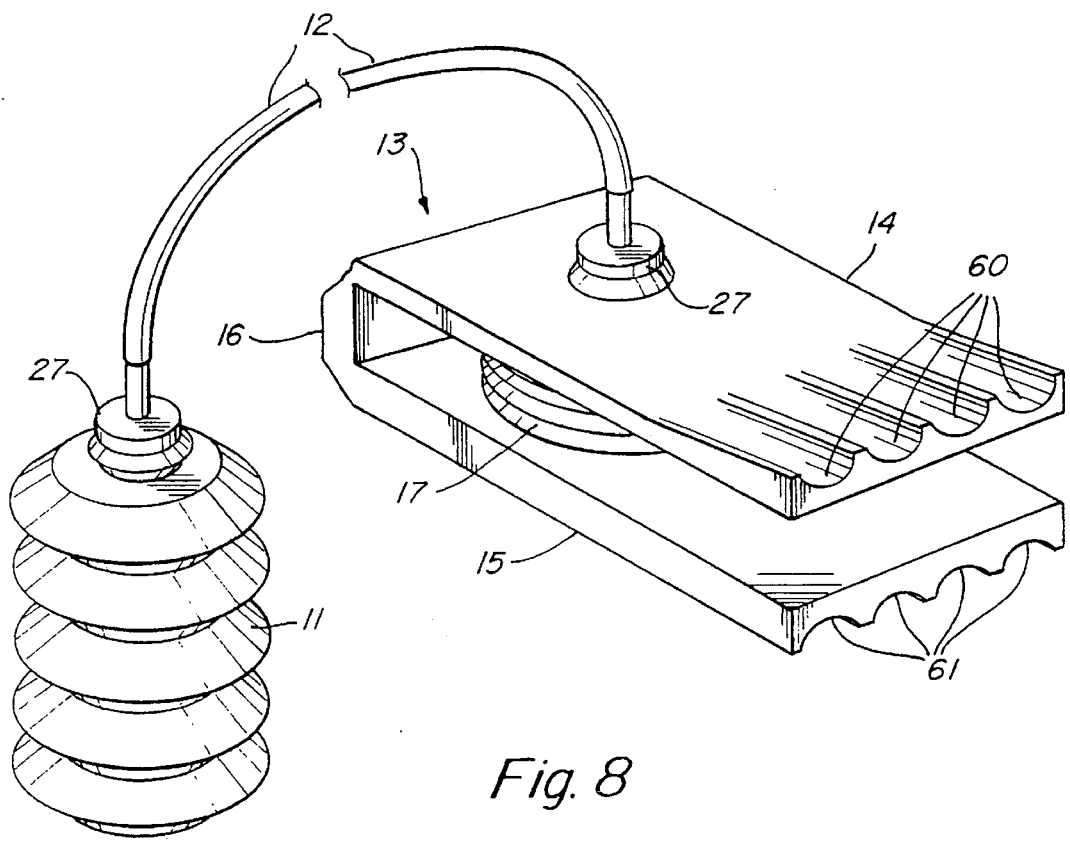
FIG. 8 is a perspective view of a hydraulic mechanism for a hand exerciser of the present invention.

Although the fluid motion device has been described in FIGS. 1–7 with respect to movement of the upper and lower jaws to exercise the temporomandibular joint or to tone jaw muscles, it is possible to modify the motion device shown in FIG. 2 for other uses by eliminating the portions thereof for holding the upper and lower teeth. FIG. 8 has finger grips 60 and 61 on the upper and lower members 14 and 15, which could be used by a person with arthritic hands to exercise the hand and finger joints in the hand. In this configuration, the person would hold the portion of the upper and lower members 14 and 15, furthest from the hinge at finger grips 60 and 61 and squeeze the fluid source 11 to expand the bellows 17, thereby exercising the hand. Similarly the modified device of FIG. 8 could easily be further modified to exercise other small joints such as one or more fingers and toes. For example, for finger exercise, a finger groove or grooves 60 would be placed for example on the top or upper member 14. The unit could then be placed on a table or other support and the user's finger or fingers could be exercised by squeezing the bellows of the fluid source 11. Maximum movement of the finger could be limited by the stop means 32, 33 of FIG. 5 or other suitable means. The position of the bellows 17 between members 14 and 15 can be altered to provide a desired mechanical advantage. For a toe exerciser, for exercising one or more toes, the size of the device shown in FIG. 8 would be scaled down to accommodate one or more toes. The scaled down device could be placed on the floor or other surface. The grips 60 would have one or more toes of a user placed therein and the toe could be exercised by squeezing fluid source 11.

Figure 9:
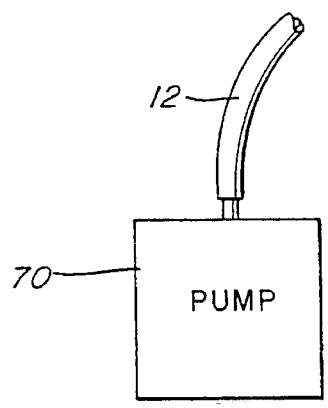
FIG. 9 is a sectional view of an infusion pump which replaces fluid source 11 and FIGS. 1, 2 and 8.

FIG. 9 is a sectional view of a portion of FIGS. 1, 2 and 8 in which the fluid source 11 is replaced by an infusion pump 70 which is connected to flexible tube 12.

Figures 10, 11:
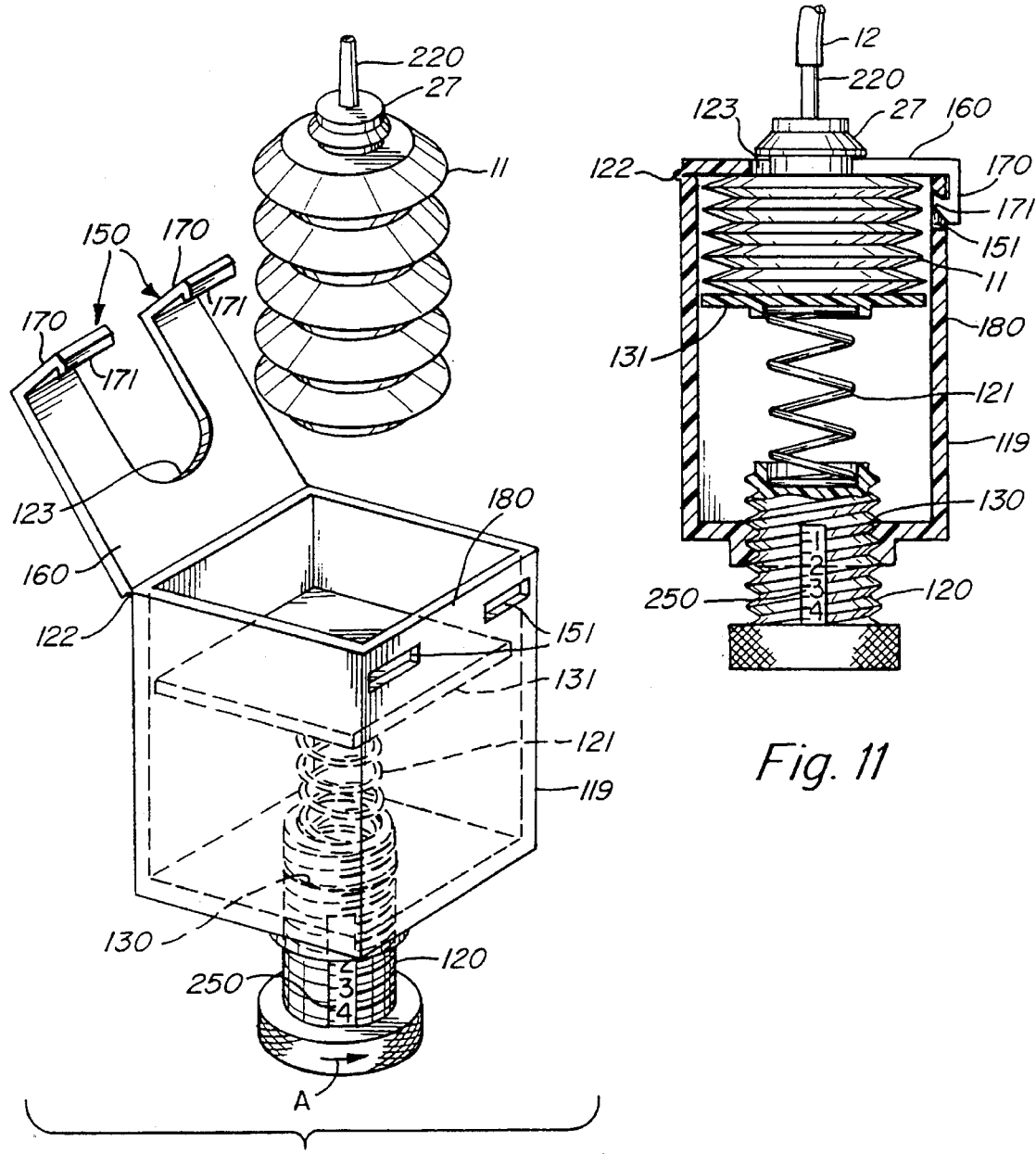
FIG. 10 is a perspective view of a first squeezing device having a housing for squeezing fluid source 11 shown in FIG. 1, in which a top hinged cover is in an open position.
FIG. 11 is a sectional view of the housing of FIG. 10, with the fluid source in place.

FIG. 10 shows a housing 119 for the bellows 11 (fluid source) shown in FIG. 1 for use of the apparatus to tone jaw muscles. The top cover 160 of housing 119 is in an open position in FIG. 10. The coupling 27 of the bellows 11 shown in FIG. 1 is inserted through the slot-like opening 123 in the top cover 160 of the housing 119 after the bellows 11 is inserted in housing 119. The tube 12 of FIG. 1 is then connected to the tubular top 220 of coupling 27 of bellows 11. A hinge 122 holds the top cover 160 of the housing 119 to the housing at an end portion thereof as shown in FIGS. 10 and 11. The housing 119 is preferably made of molded plastic and hinge 122 is preferably a molded plastic hinge (i.e., a living hinge). A threaded aperture 130 is formed in the bottom 125 of housing 119, into which a threaded adjustment member 120 is fitted. The adjustment member 120 is threaded to screw into the aperture 130 as the member 120 is turned, as shown by arrow A in FIG. 10. The threaded member 120 moves toward the interior of the housing 119 (see FIG. 11) as it is turned in a direction shown by arrow A. The spring 121 shown in FIG. 10 is mounted on the interior end portion of member 120 so that when the threaded member 120 is rotated in the direction of arrow A, the spring and flat plate-like member 131 mounted on spring 121, will exert an increasing force on the bellows 11 mounted in the housing 119 (see FIG. 11). The spring 121 can be eliminated and the threaded member can be attached directly to the flat plate-like member 131. The threaded member has a scale 250 marked thereon which shows different pressures applied to the bellows 11. The threaded member 120 is turned to provide continuously variable pressures on the bellows 11 in the housing 119.

The locking means 150 and 151 shown in FIG. 10 lock the top cover 160 of the housing into place on housing 119 and retains the bellows 11 within the housing 119. The locking means shown in FIG. 10 includes hook-like members 150 formed (i.e., molded) on an end portion on the top cover 160 which extends across the entire end portion of the top cover except where the cut-out portion 123 exists. Hook-like member 150 comprises a first member 170 which extends substantially perpendicularly from the edge portion of top cover 160. The first member 170 can be formed integrally with the top cover 160. At an end portion of the member 170 that is furthest away from top cover 160 is an inwardly extending hook member 171 which engages in hollows or apertures 151 formed in the side wall 180 of the housing 119. The hollows or apertures 151 together with hook members 171 form a snap-type closure which is readily openable. The material forming the members 170 and 171 is a resilient plastic material which will keep the top cover 160 in place when the top cover is closed. Because of this resilience, cover 160 can be snapped open by applying pressure to the members 172 or by depressing side wall 180 of the housing 119 in an area adjacent to portions 151. When the cover 160 is snapped to the closed position thereof, it will retain the bellows 11 within the housing 119 even against a pressure provided by spring 121. The spring 121 is mounted on the threaded member 120 at one end thereof and has the flat member 131 mounted at the other end thereof. The spring 121 is compressed as member 120 is turned in the direction of arrow A. The spring 121 can also resiliently yield if sufficient pressure is provided into the interior of the fluid source 11 by a pressure therein caused for example, when a user bites down on the first and second members.

As shown in FIG. 10, the threaded member 120, when rotated in the direction of arrow A moves toward an interior portion of the housing 119. The scale 250 is provided on threaded member 120. The numbers on the scale on the threaded member 120 indicate the position of the rotation of the threaded member 120.

In operation, the bellows 11 is inserted into the housing 119 and the top portion of the bellows 27 is inserted through the opening 123 of the housing 119 and the tube 12 is connected to the top portion 220 of the coupling 27 of bellows. The top cover 160 of the housing 119 is closed and locked in the closed position and the desired pressure on the bellows 11 is selected by turning threaded member 120 to provide a desired pressure on the bellows 11. The desired pressure on bellows 11 will expand the bellows 17 that is positioned adjacent the mouth of a user to expand by a preselected amount (corresponding to the interior volume of the housing 119 as determined by the position of plate 131). Pressure is then applied by the jaws of a user in an effort to try to close the user's mouth. Resistance is provided by maintaining compression of the bellows 11 with the spring 121 and plate 131 to maintain the pressure in the bellows 11. In use, the device is preferably first inserted in the mouth after the bellows 11 has been inserted in the housing 119, and then the top cover 160 of the housing 119 is closed. The pressure on the bellows 11 in turn expands the bellows 17. The amount of pressure applied to bellows 11 is determined by the setting on the scale 250. As noted above, the user then applies pressure to the bellows 17 by trying to bite down, i.e., to close the user's jaws in an effort to close the user's mouth. Resistance is provided to the bite down of the jaws by the bellows 17 not being permitted to substantially contract. The degree of resistance, as noted above, can be adjusted by the user by adjusting the pressure exerted on bellows 11 by spring 121 and adjustment member 120.

Alternatively, instead of using the housing 119, the user may compress bellows 11 by squeezing with his/her hand, which in turn inflates bellows 17. The user then bites down on the upper member 14 and the lower member 15, shown in FIG. 1. The biting down occurs against the maintained resistance provided by the manual squeezing of bellows 11, thereby toning the jaw muscles of the user adjacent to the TMJ joint.

The device as shown in FIG. 10 and FIG. 11 is used after bellows 11 is at least partially squeezed to inflate bellows 17. This provides an exercise device which enables the user to bite down on the members 14 and 15 to thereby exercise the TMJ joint when the bellows 17 is permitted to contract and provides a resistive jaw muscle toning device if bellows 17 is restrained from contracting.

Figure 12:
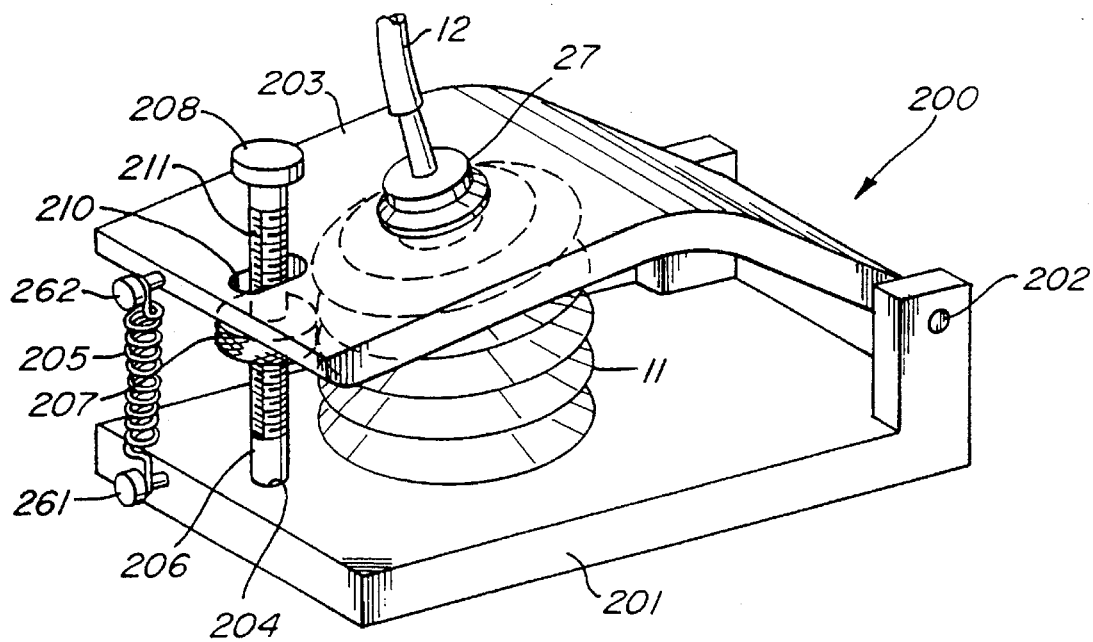
FIG. 12 is a perspective view of a second squeezing device for squeezing the fluid source 11 shown in FIG. 1, in which the second squeezing device is in a squeezed operating position.
Figure 13:
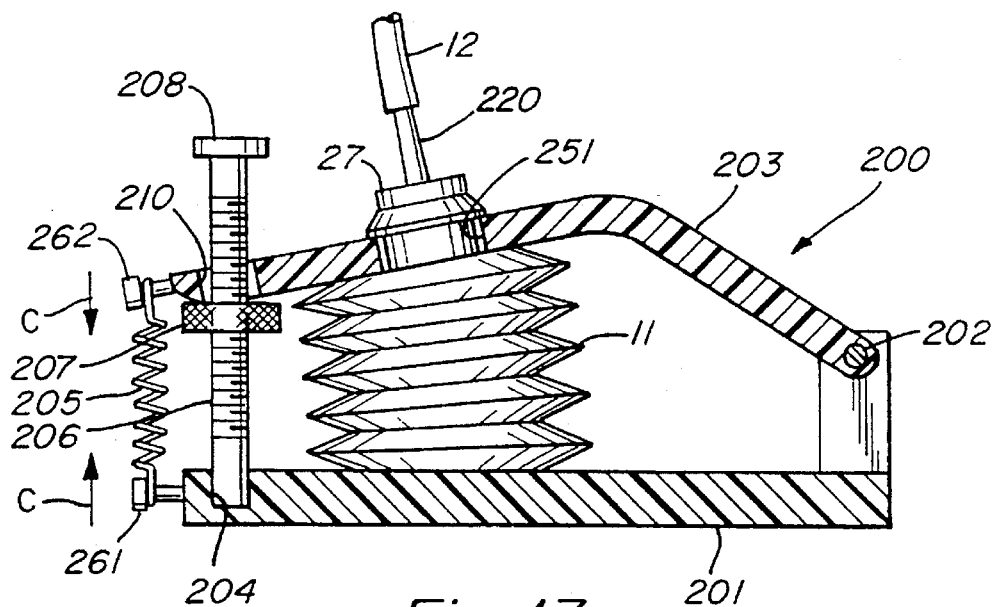
FIG. 13 is a cross-sectional view of the second squeezing device shown in FIG. 12.

FIGS. 12 and 13 show a tong-like squeezing mechanism 200 for squeezing the fluid source (bellows) 11 shown in FIG. 1. The squeezing device shown in FIGS. 12 and 13 has a first arm 201 and a second arm 203 pivotally connected together by a pivot shaft 202. The arms 201 and 203 pivot around the pivot shaft 202 so that they are movable toward or away from each other. The arm 201 has a bottom portion of the bellows 11 resting on a surface thereof. The arm 203 has an aperture 251 formed therein (see FIG. 13) through which extends the tube-end portion of bellows 11. The fluid channel 12, shown in FIG. 1, is connected to tube end 220. At the free end portion of the arm 201 is an aperture 204 into which a threaded screw 206 is fixed. The threaded screw 206 is passed through another aperture 210 formed in the arm 203 which is slightly larger than the threaded screws 206 so that the threaded screw can slide through aperture 210. An adjustable stop member 207 is threadably mounted on the threaded screw 206 so that its position on the screw 206 can be adjusted by rotating the adjustable stop member 207. An end stop member 208 is provided on the free end portion of the threaded screw 206 on the side portion of the arm 203 which faces away from the arm 201. The end stop 208 can be fixed on threaded screw member 206 or the end stop 208 can be a threaded stop member which is threaded onto threaded screw 206 so that the end stop 208 could be rotated to move the end stop toward or away from the arm 201 along the threaded screw 206. A scale 211 can be provided on the threaded screw 206 (like the scale 250 of FIGS. 10 and 11) to indicate the amount of squeezing pressure applied to the bellows 11 by the squeezing apparatus 200 shown in FIG. 12. A spring 205 (which is under tension) is fixed between the arms 201 and 203 by screws or projections 261 and 262 at a position adjacent to the threaded screw 206 for providing a compressive biasing force to arms 201 and 203. The compression of the bellows 11 up to the point of engagement of the stop 207 limits the amount to which the jaw of the user is opened. Biasing spring 205 biases the tong-like assembly to be in a closed position determined by the stop 207. This arrangement shown in FIGS. 12 and 13 eliminates a need for a user to squeeze the tong-like device with the user's hand since the assembly would be biased toward the squeezed position by the force of the spring 205 in a direction shown by arrows C. If the spring force of spring 206 is not sufficient, the user can also squeeze members 201, 203 toward each other.

Figure 14:
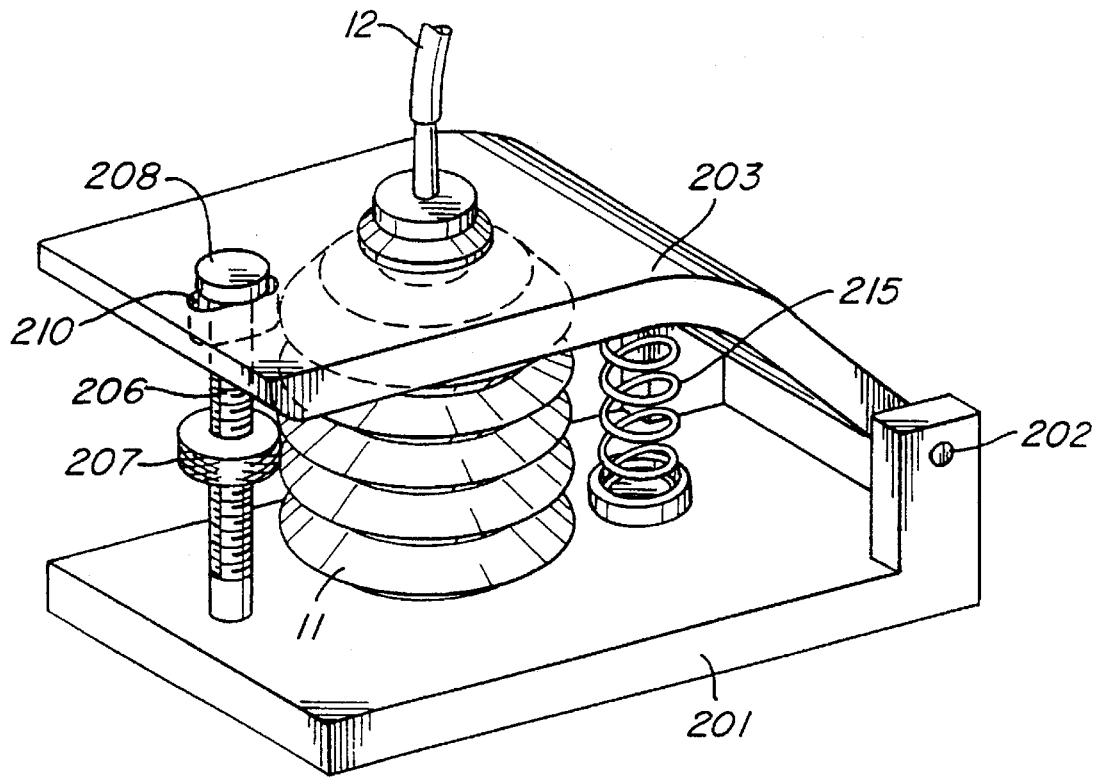
FIG. 14 is a perspective view of a modification of the second squeezing device shown in FIG. 12 in which a spring is mounted on a fulcrum side of the device between the tong arms and the fluid source 11 and in which the tong device is in an unsqueezed position.
Figure 15:
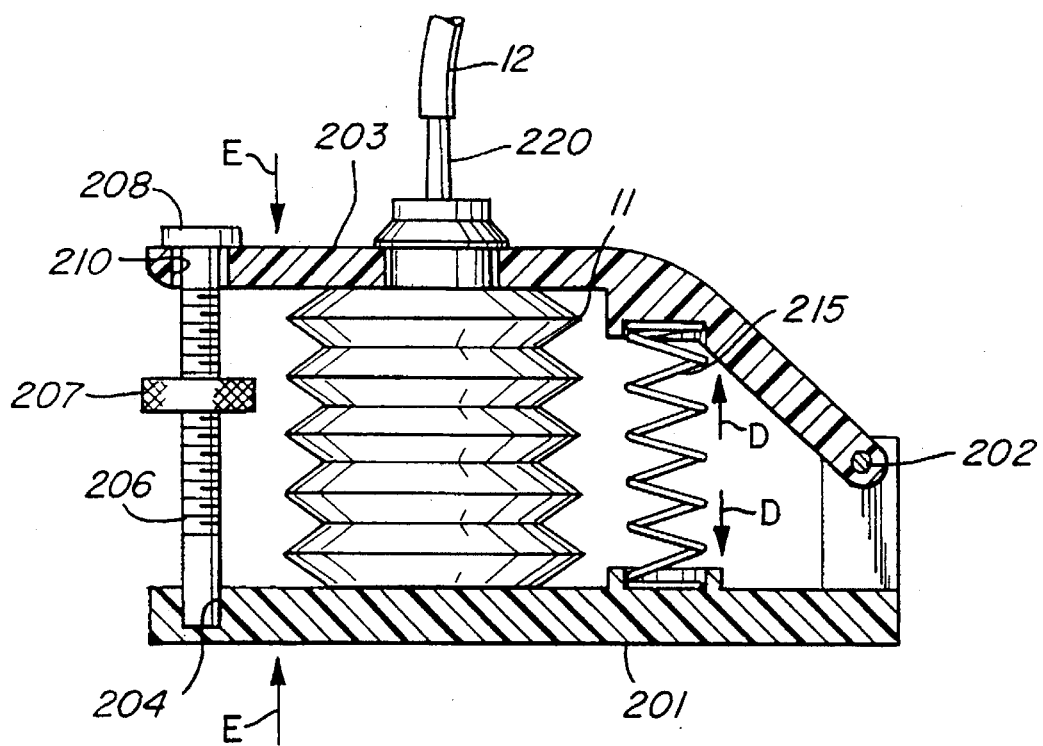
FIG. 15 is a cross-sectional view of the device shown in FIG. 14.

FIG. 14 is a perspective view of a tong-like device similar to the tong-like device shown in FIGS. 12 and 13 except that the biasing spring 215 (which is under compression) is positioned in respective recesses in members 201, 203 and between the pivot 202 and the bellows 11. In FIGS. 14 and 15 the biasing spring 205 biases the arms 201 and 203 of the tong-like device to an unoperated position where the arms 201 and 203 do not apply a pressure to the fluid source 11. In FIGS. 14 and 15 spring 215 tends to hold arms 203 and 201 open, as shown by arrows D in FIG. 15. When the arms 201 and 203 do not provide pressure on the fluid source 11 as shown in FIGS. 14 and 15, the jaws of the user are relaxed. Pressure on the arms 201 and 203 to close them to the stop 207 opens the user's jaws a desired amount. The device as shown in FIGS. 14 and 15 is used to gradually increase the range of motion of the user, similar to the device shown in FIG. 1 of the present application and would act as a replacement for the elastic member 19 shown in FIG. 3 of the present application. In FIGS. 14 and 15, the user applies a pressure in a direction of arrow E shown in FIG. 15 to apply a pressure to the bellows 11 which then expels fluid through the channel 12 to the fluid reservoir 17.

In operation, a user places the squeezing device shown in FIGS. 12–15 in his/her hand and then arms 201 and 203 are squeezed together until they reach the adjustable stop 207 or until a measured point on the scale 211 on threaded screw 206 is reached.

The squeezing of the arms 201 and 203 together will squeeze the bellows 11 to expel fluid therefrom into the fluid reservoir 17 which will inflate the fluid reservoir 17 in the user's mouth. The user will place the first and second members in his or her mouth before squeezing with the squeezing device 200. A squeezing of the squeezing device 200 as noted above, will inflate the bellows 17 adjacent the user's mouth to separate the first and second members in the user's mouth. In the toning apparatus of the present invention, after the bellows 17 has been inflated, the user bites down on the first and second members in an attempt to close the user's jaws. Since bellows 11 is receiving a pressure from the squeezing device 200 shown in FIGS. 12–15, the user's jaws will meet resilience which results from the fact that the fluid in reservoir 17 cannot easily flow into the bellows 11 because of the pressure being maintained in bellows 11. The user's jaws will be able to move somewhat as they bite down on the first and second members because of the resilience of bellows 17, the resilience of bellows 11, the resilience of the members connecting bellows 17 to bellows 11, and the compressibility of the fluid contained in the system. Bellows 11 will receive some back pressure as the bellows 17 is bitten down on by the user. This resilience nonetheless will provide sufficient pressure against the motion of the user's jaws to tone the jaw muscles of the user.

While the invention has been described with reference to the drawings and structures and method disclosed herein, it is not confined to the details set forth, and is intended to cover modifications or changes as may come within the scope of the following claims.

We claim:

1. A method for toning jaw muscles of a user, comprising:
providing first and second members which are coupled together so that at least said first member is movable relative to said second member;

providing an expandable and contractible fluid reservoir between said first and second members, such that said first and second members will move relative to each other as said reservoir expands and contracts; and expanding said fluid reservoir by forcing fluid from a fluid source into said fluid reservoir; and limiting release of fluid from said fluid reservoir when the user attempts a bite down on said first and second members, to thereby provide a controlled resistance to said bite down by said user, whereby said controlled resistance to said bite down enhances tone of jaw muscles of said user.

2. The method according to claim 1, wherein the limited releasing of fluid substantially prevents release of fluid from said expandable fluid reservoir.

3. The method according to claim 2, comprising controlling a maximum movement of said first and second members relative to each other to thereby control a maximum opening of an upper and a lower jaw of the user.

4. The method according to claim 3, wherein said controlling step comprises limiting said maximum relative movement of said first and second members to a preselected maximum value.

5. The method according to claim 3 wherein said limiting release of fluid from said fluid reservoir comprises:
providing spring means to tend to force fluid from said fluid source into said fluid reservoir, said spring means yielding when said user bites down on said first and second members to create a back pressure in said fluid source.

6. The method according to claim 1, wherein said fluid reservoir comprises a bellows.

7. The method according to claim 1, wherein said fluid source is squeezable and said expanding step comprises manually squeezing said fluid source to force fluid into said fluid reservoir.

8. The method according to claim 1, wherein said user has an upper and a lower jaw respectively having teeth ridges, further comprising:
providing hinge means acting as a fulcrum to couple said first and said second members together;
forming upper teeth ridge positioning means on said first member and lower teeth ridge positioning means on said second member;
positioning said upper and lower teeth ridge positioning means on a given side of said fulcrum; and
positioning said fluid reservoir on said given side of said fulcrum between said hinge means and said upper and said lower teeth ridge positioning means.

9. The method according to claim 8, further comprising:
sliding said upper and lower teeth ridge positioning means into a mouth of the user to engage said upper and lower teeth ridges of said user.

10. The method according to claim 1, wherein said expanding of said fluid reservoir includes forcing said fluid from said fluid source into said fluid reservoir with a preselected pressure to thereby expand said fluid reservoir a predetermined amount.

11. The method according to claim 10, wherein said preselected fluid pressure from the fluid source is selectable among a plurality of fluid pressures.

12. A fluid motion device for toning jaw muscles of a user comprising:
a fluid source;
first and second members;

hinge means for holding said first and second members together while permitting at least said first member to move relative to said second member;

an expandable and contractible fluid reservoir positioned between said first and second members;

a fluid channel connecting said fluid source and said fluid reservoir, said fluid channel providing fluid communication between said fluid source and said fluid reservoir;

means for forcing fluid from said fluid source into said fluid reservoir to expand said fluid reservoir, thereby moving apart said first and second members;

said first and second members with said fluid reservoir therebetween being insertable between an upper and a lower jaw of said user for toning jaw muscles of said user when said fluid reservoir contracts when said user closes said upper and lower jaws on said first and second members; and means for limiting release of fluid from said fluid reservoir when said user close said upper and lower jaws on said first and second members, thereby providing a resistance to closing said upper and lower jaws by said user, said resistance enhancing muscular tone of jaw muscles of said user.

13. The fluid motion device according to claim 12, further comprising controlling means for controlling a maximum opening between said first and second members.

14. The fluid motion device according to claim 13, wherein said controlling means comprises limit means for limiting said maximum opening to a given amount.

15. The fluid motion device according to claim 12, wherein said fluid reservoir comprises a bellows.

16. The fluid motion device according to claim 12, wherein said fluid source is squeezable, said fluid source forcing fluid into said fluid reservoir whenever said fluid source is squeezed.

17. The fluid motion device according to claim 16, wherein squeezing means are provided for squeezing said fluid source with a predetermined pressure to thereby expand said fluid reservoir a preselected amount.

18. The fluid motion device according to claim 16, wherein said fluid source is manually squeezable.

19. The fluid motion device according to claim 16, wherein squeezing means are provided for squeezing said fluid source with one of a plurality of predetermined pressures for expanding said fluid reservoir a preselected amount among a plurality of preselected amounts.

20. The fluid motion device according to claim 19, wherein said squeezing means comprises:

spring means for applying a squeezing force to said fluid source; and means for positioning said spring means to exert a selectable force to said fluid source.

21. The fluid motion device according to claim 20, wherein:

said fluid source is mounted in a housing; and said spring means is pressed against said fluid source when a cover of said housing is moved to a closed position.

22. The fluid motion device according to claim 21, wherein the spring means is yieldable when said user bites down on said first and second members to produce a resilient back pressure in said fluid source.

23. The fluid motion device according to claim 19, wherein said squeezing means comprises:

first and second arms pivotally connected to each other to enable said first and second arms to move toward and away from each other;

the fluid source being mounted between said first and second arms;

stop means for limiting a movement of said first and second arms toward each other; and means for preventing said first and second arms for moving more than a predetermined distance apart from each other.

24. The fluid motion device according to claim 23, wherein said stop means comprises:

a threaded screw fixedly mounted in one of said first and second arms; and a stop member adjustably mounted on said threaded screw.

25. The fluid motion device according to claim 24, wherein the other of the first and second arms has an aperture therethrough, said threaded screw being slidable through said aperture.

26. The fluid motion device according to claim 25, wherein said preventing means comprises a member coupled to a free and portion of said threaded screw.

27. The fluid motion device according to claim 25, wherein said preventing means comprises a threaded rotatable adjusting member mounted on a free end portion of said threaded screw for adjusting a position of said preventing means.

28. The fluid motion device according to claim 24, further comprising scale means for indicating a pressure applied to said fluid source.

29. The fluid motion device according to claim 23, further comprising spring means coupled between said first and second arms.

30. The fluid motion device according to claim 29, wherein said spring means comprises a tension spring for moving said arms toward each other.

31. The fluid motion device according to claim 29, wherein said spring means comprises a compression spring for moving said arms apart from each other.

32. The fluid motion device according to claim 29, wherein said spring means is mounted to free end portions of said first and second arms.

33. The fluid motion device according to claim 29, wherein said spring means is mounted between a pivot coupling said first and second arms together and said fluid source mounted between said first and second arms.

34. The fluid motion device according to claim 12, wherein each of said upper and lower jaws has teeth ridges, further comprising:

upper teeth ridge positioning means mounted on said first member; and lower teeth ridge positioning means mounted on said second member;

said hinge means acting as a fulcrum to hold said first and said second members together;

both said upper and lower teeth ridge positioning means being positioned on a given side of said fulcrum; and said fluid reservoir being positioned on said given side of said fulcrum between said hinge means and said upper and lower teeth ridge positioning means.

35. The fluid motion device according to claim 12, wherein said hinge means comprises a double acting hinge which provides limited lateral movement of said first and second members relative to each other to thereby compensate for overbite or underbite of a user.

36. The fluid motion device according to claim 35, further comprising first and second protrusions formed on said double acting hinge, a third protrusion formed on said first member and a fourth protrusion formed on said second member, said first and third and second and fourth protrusion being positioned to limit lateral and vertical movement of said double acting hinge.

37. The fluid motion device according to claim 12, wherein said fluid channel is permanently sealed.

38. The fluid motion device according to claim 12, wherein said fluid source, said fluid reservoir, and said fluid communication channel are all formed of a flexible plastic.

* * * * *